United States Patent [19]

Laurent et al.

[11] Patent Number: 4,515,780

[45] Date of Patent: May 7, 1985

[54] ANIMAL NUTRITION

[75] Inventors: Sebastian M. Laurent, Greenwell Springs, La.; Wilson G. Pond, Hastings, Nebr.

[73] Assignees: Ethyl Corporation, Richmond, Va.; The United States of America as represented by the Secretary of Agriculture, Washington, D.C.

[21] Appl. No.: 497,657

[22] Filed: May 24, 1983

[51] Int. Cl.$^3$ .............................................. A61K 33/06
[52] U.S. Cl. ..................................................... 424/154
[58] Field of Search ................................ 424/154, 157

[56] References Cited

U.S. PATENT DOCUMENTS 3,836,676  9/1974  Komakine ............................. 424/74
4,393,082  7/1983  White et al. ............................ 426/2

OTHER PUBLICATIONS

"Ethyl Eza zeolite A", pamphlet.
Nongsa Sihom Youngu Pogo 1978, 20 (Livestock), pp. 77–83.
Mumpton, et al.–*Journal of Animal Science,* vol. 45, No. 5, (1977), pp. 1188–1203.

*Primary Examiner*—Frederick E. Waddell
*Attorney, Agent, or Firm*—Donald L. Johnson; John F. Sieberth; Paul H. Leonard

[57] ABSTRACT

A feed formulation for animals, particularly ruminant animals, and especially sheep, containing a small amount of zeolite.

A method of inhibiting the formation of kidney stones or urinary calculi in animals, wherein a small amount of zeolite, especially synthetic zeolite A, up to about five weight percent is added to a feed formulation otherwise containing sufficient nutrients, for said animals.

12 Claims, No Drawings

ANIMAL NUTRITION

BACKGROUND OF THE INVENTION

The present invention is in the general field of animal feeding and relates particularly to the feeding of ruminant animals, especially sheep.

With the continuing growth of world population, it is increasingly important that effective means be found for increasing the food supply. One means of doing this is to increase the production of the animals which are a major source of human nutritional needs. Ruminant animals comprise a substantial part of the total food stock.

One serious problem with raising ruminant animals, particularly sheep, is the formation of kidney or bladder stones in the animals. Excessive formation of such stones causes premature death of affected animals.

Urinary stones are also found in fairly high incidence in domestic animals such as cats and dogs. The problem is especially severe in male cats that have been neutered. The stones not only cause great pain or even death to the affected animal, and mental pain and anguish to their owners, they also create financial burdens for the latter. In addition to expenses for medical treatments, more expensive and carefully selected pet foods must be fed to the animal susceptible to stones in the urinary tract. It has been unexpectedly discovered that the addition of a small amount of zeolite, such as a zeolite A, to the animals regular feed will effectively reduce or inhibit the formation of such stones or urinary calculi.

Zeolites are crystalline, hydrated aluminosilicates of alkali and alkaline earth cations, having infinite, three-dimensional structures.

Zeolites consist basically of a three-dimensional framework of $SiO_4$ and $AlO_4$ tetrahedra. The tetrahedra are crosslinked by the sharing of oxygen atoms so that the ratio of oxygen atoms to the total of the aluminum and silicon atoms is equal to two or $O/(Al+Si)=2$. The electrovalence of each tetrahedra containing aluminum is balanced by the inclusion in the crystal of a cation, for example, a sodium ion. This balance may be expressed by the formula $Al/Na=1$. The spaces between the tetrahedra are occupied by water molecules prior to dehydration.

Zeolites A may be distinguished from other zeolites and silicates on the basis of their composition and X-ray powder diffraction patterns and certain physical characteristics. The X-ray patterns for these zeolites are described below. The composition and density are among the characteristics which have been found to be important in identifying these zeolites.

The basic formula for all crystalline sodium zeolites may be represented as follows:

$Na_2O.Al_2O_3.xSiO_2.yH_2O.$

In general, a particular crystalline zeolite will have values for "x" and "y" that fall in a definite range. The value "x" for a particular zeolite will vary somewhat since the aluminum atoms and the silicon atoms occupy essentially equivalent positions in the lattice. Minor variations in the relative number of these atoms do not significantly alter the crystal structure or physical properties of the zeolite. For zeolite A, the "x" value normally falls within the range $1.85\pm0.5$.

The value for "y" is not necessarily an invariant for all samples of zeolites. This is true because various exchangeable ions are of different size, and, since there is no major change in the crystal lattice dimensions upon ion exchange, the space available in the pores of the zeolite to accommodate water molecules varies.

The average value for "y" for zeolite A is 5.1. The formula for zeolite A may be written as follows:

$1.0\pm0.2Na_2O.Al_2O_3.1.85\pm0.5SiO_2.yH_2O.$

In the formula, "y" may be any value up to 6.

An ideal zeolite A has the following formula:

$(NaAlSiO_4)_{12}.27H_2O$

Among the ways of identifying zeolites and distinguishing them from other zeolites and other crystalline substances, the X-ray powder diffraction pattern has been found to be a useful tool. In obtaining the X-ray powder diffraction patterns, standard techniques are employed. The radiation is the $K\alpha$ doublet of copper and a Geiger counter spectrometer with a strip chart pen recorder is used. The peak heights, I, and the positions as a function of $2\theta$ where $\theta$ is the Bragg angle, are read from a spectrometer chart. From these, the relative intensities, $100\ I/I_o$, where $I_o$ is the intensity of the strongest line or peak and d the interplanar spacing in angstroms corresponding to the recorded lines are calculated.

X-ray powder diffraction data for a sodium zeolite A are given in Table I.

TABLE I
X-RAY DIFFRACTION PATTERN FOR ZEOLITE A

| $h^2 + k^2 + l^2$ | d (Å) | $\dfrac{100\ I}{I_o}$ |
|---|---|---|
| 1 | 12.29 | 100 |
| 2 | 8.71 | 70 |
| 3 | 7.11 | 35 |
| 4 | 6.15 | 2 |
| 5 | 5.51 | 25 |
| 6 | 5.03 | 2 |
| 8 | 4.36 | 6 |
| 9 | 4.107 | 35 |
| 10 | 3.895 | 2 |
| 11 | 3.714 | 50 |
| 13 | 3.417 | 16 |
| 14 | 3.293 | 45 |
| 16 | 3.078 | 2 |
| 17 | 2.987 | 55 |
| 18 | 2.904 | 10 |
| 20 | 2.754 | 12 |
| 21 | 2.688 | 4 |
| 22 | 2.626 | 20 |
| 24 | 2.515 | 6 |
| 25 | 2.464 | 4 |
| 26 | 2.414 | >1 |
| 27 | 2.371 | 3 |
| 29 | 2.289 | 1 |
| 30 | 2.249 | 3 |
| 32 | 2.177 | 7 |
| 33 | 2.144 | 10 |
| 34 | 2.113 | 3 |
| 35 | 2.083 | 4 |
| 36 | 2.053 | 9 |
| 41 | 1.924 | 7 |
| 42 | 1.901 | 4 |
| 44 | 2.858 | 2 |
| 45 | 1.837 | 3 |
| 49 | 1.759 | 2 |
| 50 | 1.743 | 13 |
| 53 | 1.692 | 6 |
| 54 | 1.676 | 2 |
| 55 | 1.661 | 2 |
| 57 | 1.632 | 4 |

TABLE I-continued

| X-RAY DIFFRACTION PATTERN FOR ZEOLITE A | | |
|---|---|---|
| $h^2 + k^2 + l^2$ | d (Å) | $\frac{100\ I}{I_o}$ |
| 59 | 1.604 | 6 |

The more significant d values for zeolite A are given in Table II.

TABLE II

| MOST SIGNIFICANT d VALUES FOR ZEOLITE A |
|---|
| d Value of Reflection in A |
| 12.2 ± 0.2 |
| 8.7 ± 0.2 |
| 7.10 ± 0.15 |
| 5.50 ± 0.10 |
| 4.10 ± 0.10 |
| 3.70 ± 0.07 |
| 3.40 ± 0.06 |
| 3.29 ± 0.05 |
| 2.98 ± 0.05 |
| 2.62 ± 0.05 |

Occasionally, additional lines not belonging to the pattern for the zeolite appear in a pattern along with the X-ray lines characteristic of that zeolite. This is an indication that one or more additional crystalline materials are mixed with the zeolite in the sample being tested. Small changes in line positions may also occur under these conditions. Such changes in no way hinder the identification of the X-ray patterns as belonging to the zeolite.

The particular X-ray technique and/or apparatus employed, the humidity, the temperature, the orientation of the powder crystals and other variables, all of which are well known and understood to those skilled in the art of X-ray crystallography or diffraction can cause some variations in the intensities and positions of the lines. These changes, even in those few instances where they become large, pose no problem to the skilled X-ray crystallographer in establishing identities. Thus, the X-ray data given herein to identify the lattice for a zeolite, are not to exclude those materials which, due to some variable mentioned or otherwise known to those skilled in the art, fail to show all of the lines, or show a few extra ones that are permissible in the cubic system of that zeolite, or show a slight shift in position of the lines, so as to give a slightly larger or smaller lattice parameter.

A simpler test described in "American Mineralogist," Vol. 28, page 545, 1943, permits a quick check of the silicon to aluminum ratio of the zeolite. According to the description of the test, zeolite minerals with a three-dimensional network that contains aluminum and silicon atoms in an atomic ratio of $Al/Si = \frac{2}{3} = 0.67$, or greater, produce a gel when treated with hydrochloric acid. Zeolites having smaller aluminum to silicon ratios disintegrate in the presence of hydrochloric acid and precipitate silica. These tests were developed with natural zeolites and may vary slightly when applied to synthetic types.

U.S. Pat. No. 2,882,243 describes a process for making zeolite A comprising preparing a sodium-aluminum-silicate water mixture having an $SiO_2:Al_2O_3$ mole ratio of from 0.5:1 to 1.5:1, and $Na_2O/SiO_2$ mole ratio of from 0.8:1 to 3:1, and an $H_2O/Na_2O$ mole ratio of from 35:1 to 200:1, maintaining the mixture at a temperature of from 20° C. to 175° C. until zeolite A is formed, and separating the zeolite A from the mother liquor.

It is therefore a principal object of the present invention to provide a feed formulation for more effective use of zeolites, especially zeolite A in animal feeds or in an animal's diet, particularly in the diets of ruminant animals, especially sheep.

It is an important object of the present invention to provide an improved feed formulation for animals which contains a small amount of zeolite A.

It is another object of the invention to provide an animal feed containing zeolite A which effectively inhibits the formation of kidney stones or urinary calculi in animals.

Still another object of the invention is to cost effectively increase the production of animals slaughtered for food.

Yet a further object of the present invention is to provide an improve feed formulation for domestic animals such as cats and dogs which effectively inhibits the formation of kidney stones or urinary calculi in the domestic animal.

Other objects and advantages of the invention will be more fully understood from a reading of the description and claims hereinafter.

SUMMARY OF THE INVENTION

The present invention relates to a feed formulation for animals which contains a small amount of a zeolite such as zeolite A wherein a small amount of such zeolite is added to the feed formulation and in a sufficient amount to inhibit the formation of kidney stones or urinary calculi in the animal feed.

DESCRIPTION OF THE PREFERRED EMBODIMENT

It has been discovered that the addition of a relatively small amount of zeolite to a regular or standard feed for growing sheep or lambs effectively inhibits the production of kidney stones in the animals. The zeolite is preferably added in amounts of up to about five percent of weight of the total feed.

A synthetic zeolite A, especially a sodium zeolite A is preferred. Potassium zeolite A and calcium zeolite A are also suitable.

Zeolite A is more preferably added to the feed formulation in small amounts by weight percent of up to about three. Greater amounts may be used, but may deprive the animals of the desired amount of nutrients. Greater amounts are also likely to be cost ineffective. A preferred amount of zeolite A is from about 0.25 to about three percent by weight of the total feed formulation. A most preferred amount of zeolite A is about 2.00 to about 3.00 weight percent of the total feed formulation.

Diets fed to the sheep preferably consist principally of corn supplemented with alfafa hay, a soybean meal (SBM), fish meal, urea, or combinations of these.

Among ruminant animals, sheep are prone to formation of urinary calculi. Lamb feeding studies were conducted which show beneficial responses in the prevention or inhibition of stones formation when synthetic zeolite A is contained in the diet. In the initial study four lambs died during testing and three others were found to have serious stone conditions after slaughter at the end of the test period. Of the seven sheep, four were controls and three had been fed a low purity clinoptilolite, a natural zeolite mineral. Examination after slaughter revealed that one lamb which had been fed zeolite A had a very tiny "sand grain" in its bladder. The grain was too small to retrieve and was not analyzed.

In another test, three of the control animals and one of the clinoplolite fed animals died. None of the lambs fed zeolite A showed urinary calculi problems. No bladder inspections were made after this test group was slaughtered.

Stones from the first test were analyzed by X-ray diffraction and were identified as magnesium-potassium phosphate hexahydrate ($MgKPO_4.6H_2O$). This stone is isomorphous in its crystalline structure with the mineral struvite ($MgNH_4PO_4.6H_2O$). Such stone is a common urinary calculus in canines, felines and humans. Insoluble phosphate stones of this type are more common in sheep than in other ruminants. Dairy cattle have the next highest incidence of kidney stones, which is probably attributable to their normally longer life. Beef cattle kept in feed lots experience a higher incidence of stones than when allowed to graze.

In the initial testing program 54 lambs were individually housed and individually fed. Three basal diets were used as follows:
 a. Corn—a low protein diet (9% protein)
 b. Corn plus urea—(15% protein)
 c. Corn+soybean meal (SBM)—(15% protein)

For comparative purposes, 3% zeolite A and 3% clinoptilolite (CLIN) were added to each of the three basal feeds. The diets are detailed in Table III hereinafter.

The zeolite A was a commercial zeolite identified as EZA ® zeolite A. The sodium content of the zeolite is about 12.9 percent by weight.

The clinoptilolite was Double Eagle finely pulverized material (<50 mesh) from Buckhorn, N. Mex. Analysis indicated a crystallinity of 58 percent.

The testing program was conducted over a nine week period with six lambs being fed on each of nine diets.

The caloric level of the nine diets was identical. The corn-urea and corn-SBM diets were isonitrogenous.

TABLE III

| | COMPOSITION OF DIETS (PELLETED) | | | | | | | | |
|---|---|---|---|---|---|---|---|---|---|
| | Diet No.* | | | | | | | | |
| | (a) | | | (b) | | | (c) | | |
| Ingredient | 1 | 2 | 3 | 4 | 5 | 6 | 7 | 8 | 9 |
| | Weight Percent of Composition | | | | | | | | |
| Alfalfa hay** | 12.5 | 12.5 | 12.5 | 12.5 | 12.5 | 12.5 | 12.5 | 12.5 | 12.5 |
| Corn | 86.55 | 83.55 | 83.55 | 83.55 | 80.85 | 80.85 | 72.55 | 69.55 | 69.55 |
| Soybean meal (44% CP) | — | — | — | — | — | — | 14.0 | 14.0 | 14.0 |
| Trace mineralized salt | 0.4 | 0.4 | 0.4 | 0.4 | 0.4 | 0.4 | 0.4 | 0.4 | 0.4 |
| Dicalcium Phosphate | 0.5 | 0.5 | 0.5 | 0.5 | 0.5 | 0.5 | 0.5 | 0.5 | 0.5 |
| Viatmin A, D and E premix | 0.05 | 0.05 | 0.05 | 0.05 | 0.05 | 0.05 | 0.05 | 0.05 | 0.05 |
| Urea | — | — | — | 2.7 | 2.7 | 2.7 | — | — | — |
| Clinoptilolite | — | 3.0 | — | — | 3.0 | — | — | 3.0 | — |
| Zeolite A | — | — | 3.0 | — | — | 3.0 | — | — | 3.0 |
| TOTAL | 100.0 | 100.0 | 100.0 | 100.0 | 100.0 | 100.0 | 100.0 | 100.0 | 100.0 |

*As fed basis
**Sun cured pellets

The feeding tests are summarized in Table IV.

TABLE IV

| | SUMMARY OF FEEDING TESTS | | | | | | | | |
|---|---|---|---|---|---|---|---|---|---|
| | Corn | | | Corn + Urea | | | Corn + SMA | | |
| Diet No. | 1 | 2 | 3 | 4 | 5 | 6 | 7 | 8 | 9 |
| Daily Wt. gain (grams) | 302 | 327 | 227 | 370 | 302 | 254 | 368 | 340 | 375 |
| Feed intake (kg/day) | 1.695 | 1.505 | 1.323 | 1.858 | 1.554 | 1.366 | 1.680 | 1.580 | 1.813 |
| Feed efficiency* | 0.178 | 0.224 | 0.177 | 0.199 | 0.200 | 0.192 | 0.219 | 0.222 | 0.213 |

* $\frac{Wt.\ gain}{feed\ intake} \times 0.97$ (adjustment for 3% zeolite content); except in 1, 4, 7.

During the nine week feeding program four lambs died prematurely because of kidney/bladder obstruction. Organ examination of remaining lambs slaughtered at end of program revealed that three others had severe kidney stone problems. The severity of the kidney stones as revealed by organ examination is seen in Table V.

TABLE V

| | Severity of Kidney Stone Condition | |
|---|---|---|
| Diet No. | No. of Lambs At Test End | Results and Bladder Conditions (out of 6 lambs/diet) |
| 1 | 6 | 0 (no urinary calculi) |
| 2 | 5 | 1 animal died |
| 3 | 6 | 0 |
| 4 | 5 | 1 died; 1 showed serious stone condition |
| 5 | 6 | 0 |
| 6 | 6 | 0 |
| 7 | 5 | 1 died; 1 had serious stone condition |
| 8 | 5 | 1 died; 1 had serious stone condition |
| 9 | 6 | 1 very tiny "sand grain". |

A second testing program was conducted with 63 lambs which were fed nine different feed formulations over a period of 12 weeks.

In this program, 2% zeolite A and 2% clinoptilolite were added to three basal feed formulations as follows:
 (d) corn—(10% protein)
 (e) corn plus soybean mean (SBM) (15.2% protein)
 (f) corn plus soybean mean and fish meal (15.2% protein).

The diets are detailed in Table VI hereinafter.

The results were similar to the earlier feeding trials except in this series only four animals died, three controls and one fed climoptilolite. Animals fed zeolite A showed no evidence of stone formation.

TABLE VI

COMPOSTION OF DIETS

| Ingredient | International Feed No. | Diet No. (d) 10 | 11 | 12 | (e) 13 | 14 | 15 | (f) 16 | 17 | 18 |
|---|---|---|---|---|---|---|---|---|---|---|
| | | Weight Percent of Composition | | | | | | | | |
| Alfalfa meal | 1-00-023 | 12.5 | 12.5 | 12.5 | 12.5 | 12.5 | 12.5 | 12.5 | 12.5 | 12.5 |
| Corn | 4-01-935 | 84.85 | 82.85 | 82.85 | 73.55 | 71.35 | 71.15 | 71.05 | 68.85 | 68.65 |
| Soybean meal | 5-04-604 | — | — | — | 7.0 | 7.2 | 7.4 | 14.0 | 14.2 | 14.4 |
| Menhaden fish meal | 5-02-009 | — | — | — | 5.0 | 5.0 | 5.0 | — | — | — |
| Trace mineralized salt | — | .4 | .4 | .4 | .4 | .4 | .4 | .4 | .4 | .4 |
| Calcium phosphate | 06-01-080 | 1.0 | 1.0 | 1.0 | — | — | — | .6 | .6 | .6 |
| Vitamin ADE premix | — | .05 | .05 | .05 | .05 | .05 | .05 | .05 | .05 | .05 |
| Clinoptilolite | — | — | 2.0 | — | — | 2.0 | — | — | 2.0 | — |
| Zeolite A | — | — | — | 2.0 | — | — | 2.0 | — | — | 2.0 |
| Limestone | — | 1.1 | 1.2 | 1.2 | 1.0 | 1.0 | 1.0 | 1.4 | 1.4 | 1.4 |
| Total, % | | 100.00 | 100.00 | 100.00 | 100.00 | 100.00 | 100.00 | 100.00 | 100.00 | 100.00 |
| Calculated protein, %** | | 10.2 | 10.0 | 10.0 | 15.2 | 15.2 | 15.2 | 15.2 | 15.2 | 15.2 |

**Based on US-Canada Feed Composition Tables, 3rd ed., 1982. Corn, 9.3; alfalfa meal, 17.3; soybean meal, 44.6; Menhaden fish meal, 61.1% crude protein.

The results herein are unexpected since an earlier reported study with rats indicated that zeolite A levels exceeding 0.125 weight percent increased the amount of silicon excreted in the urine leading to high levels of urinary particulate silicon, and finally aggregation to form bladder and kidney stones. Please see "Report to the Great Lakes Science Advisory Board of the International Joint Commission on the Health Implication of Non-NTA Detergent Builders," October 1980.

The forgoing disclosure and description of the invention is illustrative and explanatory thereof and various changes in the illustrated process may be made within the scope of the appended claims without departing from the spirit of the invention.

What is claimed is:

1. A method of inhibiting the formation of urinary calculi in animals, wherein a small amount of synthetic zeolite A up to about five percent by weight is added to the regular feed composition fed to the animals and said feed composition is subsequently regularly fed to the animals.

2. The method of claim 1, wherein the animals treated or fed are ruminant animals.

3. The method of claim 1, wherein the animals treated or fed are sheep.

4. The method of claim 1, wherein the animals treated or fed are canine.

5. The method of claim 1, wherein the animals treated or fed are feline.

6. The method of claim 1, wherein the animals treated or fed are bovine.

7. A method of inhibiting the formation of kidney stones or urinary calculi in animals wherein a small amount of synthetic sodium zeolite A, in an amount up to about three percent of the total amount of the food regularly fed to the animal, is fed to the animal in said regularly fed food.

8. The method of claim 7, wherein the animals are ruminant animals.

9. The method of claim 7, wherein the animals are sheep.

10. The method of claim 7, wherein the animals are bovine.

11. The method of claim 7, wherein the animals are canine.

12. The method of claim 7, wherein the animals are feline.

* * * * *